US00RE47128E

(19) United States
(12) Reissued Patent
Webster et al.

(10) Patent Number: US RE47,128 E
(45) Date of Reissued Patent: Nov. 20, 2018

(54) **PLANT TREATMENT COMPOSITIONS PARTICULARLY EFFECTIVE IN THE CONTROL OF *HETERANTHERA LIMOSA* ON RICE CROPS, AND METHODS FOR THEIR USE**

(71) Applicant: Canyon Group LLC, Yuma, AZ (US)

(72) Inventors: Eric Paige Webster, Baton Rouge, LA (US); Dominic Frank Alonso, Linden, CA (US); Sergio Comparini, Yuma, AZ (US); Wallace Keith Majure, West Monroe, LA (US); Sandra Alcaraz, Yuma, AZ (US); Charles Paul Grasso, Yuma, AZ (US); Eric James McEwen, Westwood Hills, KS (US); Tak Wai Cheung, Yuma, AZ (US)

(73) Assignee: Canyon Group LLC, Yuma, AZ (US)

(21) Appl. No.: 15/140,967

(22) Filed: Apr. 28, 2016

Related U.S. Patent Documents

Reissue of:
(64) Patent No.: 8,791,049
Issued: Jul. 29, 2014
Appl. No.: 12/966,542
Filed: Dec. 13, 2010

U.S. Applications:
(60) Provisional application No. 61/287,420, filed on Dec. 17, 2009.

(51) Int. Cl.

| | |
|---|---|
| ***A01N 43/64*** | (2006.01) |
| ***C07D 251/40*** | (2006.01) |
| ***C07D 239/42*** | (2006.01) |
| ***A01N 43/54*** | (2006.01) |
| ***A01N 43/82*** | (2006.01) |
| ***A01N 47/10*** | (2006.01) |
| ***A61K 31/53*** | (2006.01) |
| ***C07D 401/04*** | (2006.01) |
| ***A01N 43/66*** | (2006.01) |

(52) U.S. Cl.
CPC ..... *A01N 43/66* (2013.01)

(58) Field of Classification Search
CPC ..... A01N 43/66
See application file for complete search history.

(56) References Cited

U.S. PATENT DOCUMENTS

| | | | | |
|---|---|---|---|---|
| 5,798,317 | A * | 8/1998 | Pappas-Fader et al. | 504/128 |
| 5,990,047 | A | 11/1999 | Hacker et al. | |
| 7,432,226 | B2 | 10/2008 | Ziemer et al. | |
| 8,791,049 | B2 | 7/2014 | Webster et al. | |
| 2009/0215625 | A1 * | 8/2009 | McElroy et al. | 504/107 |

FOREIGN PATENT DOCUMENTS

| | | | |
|---|---|---|---|
| WO | WO-97/08164 | A1 | 3/1997 |
| WO | WO-2009/015064 | A2 | 1/2009 |

OTHER PUBLICATIONS

Decision Granting Institution of *Inter Partes* Review, Case IPR2016-00076 dated May 2, 2016.
Maryadele J. O'Neil et al., "The Merck Index, Fourteenth Edition," Merck & Co., Inc., 2006, pp. 1-8.
Declaration of Harold M. Hackworth, submitted with Petition for *Inter Partes* Review of U.S. Pat. No. 8,791,049, executed on Mar. 9, 2015 (with Appendices 1-5), pp. 1-133.
Declaration of Robert C. Scott, submitted with Petition for *Inter Partes* Review of U.S. Pat. No. 8,791,049, executed on Nov. 22, 2014, pp. 1-2.
GWN-3061 (Halosulfuron-methyl) Herbicide, U.S. Environmental Protection Agency Label issued Jul. 11, 2005, pp. 1-21.
GWN-3124, Letter from U.S. Environmental Protection Agency, dated Feb. 28, 2008, pp. 1-3.
Herbicide Handbook, "Weed Science Society of America," Ninth Edition, 2007, pp. 1-3.
University of Arkansas Division of Agriculture, Publications List, Publications Found: 1296, http://www.uaex.edu/Other_Areas/publications/publications_list.asp, updated Jan. 6, 2009, pp. 1-35.
University of Arkansas Division of Agriculture, Publications List, Publications Found: 1409, http://www.uaex.edu/Other_Areas/publicalions_list.asp, updated Apr. 30, 2010, pp. 1-38.
University of Arkansas Division of Agriculture, Publications List, Publications Found: 1657, http://www.uaex.edu/publications/order.aspx, updated Jul. 8, 2015, pp. 1-104.
University of Arkansas, Crop, Soil & Environmental Sciences, Bob Scott, Professor, Extension Weed Science, http://cses.uark.edu/1945.php, last accessed Jul. 6, 2015, pp. 1-8.
National Pesticide Information Retrieval System, EPA Registration No. 81880-26, Active Ingredients: Halosulfuron-methyl (128721), Thifensulfuron (128845), http://ppis.ceris.purdue.edu/product.aspx, Approval Date Jun. 23, 2011, 1 page.
Doug Roth, Letter from Aceto Corporation re: Aceto Corporation Offer-to-Pay Oct. 16, 2014, 1 page.
AgroNews, "Nissan Chemical to boost offshore sales agrochemicals," http://news.agropages.com/News/NewsDetail-4227.htm, Jun. 7, 2011, pp. 1-2.
49639000 Aceto Corporation Submission of Product Chemistry and Toxicity Data in Support of the Application for Registration of Halomax Plus Herbicide. Transmittal of 9 Studies. Chemical: Halosulfuron-Methyl, Date of Search: Jun. 12, 2015, pp. 1-11.
S. R. Colby, "Calculating Synergistic and Antagonistic Responses of Herbicide Combinations," Weed Science Society of America, Weeds, vol. 15, No. 1, Jan. 1967, pp. 20-22.
Doug Roth, Letter from Aceto Corporation re: Aceto Corporation Offer-to-Pay, Jul. 10, 2015, 1 page.

(Continued)

*Primary Examiner* — Bruce Campell
(74) *Attorney, Agent, or Firm* — Arent Fox LLP

(57) ABSTRACT

Provided are improved agricultural processes for the improved cultivation of rice wherein the crops are treated to control undesired vegetative growth using a plant treatment composition comprising both halosulfuron and thifensulfuron to provide improved herbicidal efficacy against Heteranthera limosa, commonly referred to as "duck salad". Also provided are compositions useful in the improved agricultural processes, as well as herbicidal treatment regimens. Unexpectedly high rates of efficacy against Heteranthera limosa, amongst rice plant in rice crops are disclosed.

43 Claims, No Drawings

(56) References Cited

OTHER PUBLICATIONS

U.S. Appl. No. 61/287,420, filed Dec. 17, 2009, pp. 1-32.
Final Written Decision, *Aceto Agriculture Chemicals Corp.*, v. *Gowan Company, L.L.C.*, Case IPR2016-00076, U.S. Pat. No. 8,791,049B2, Entered: Apr. 28, 2017.
Order: Motion to Correct Typographical Error, *Aceto Agriculture Chemicals Corp.*, v. *Gowan Company, L.L.C.*, IPR2016-00076, U.S. Pat. No. 8,791,049B2, Entered: Jul. 21, 2016, pp. 1-5.
Patent Owner's Response, *Aceto Agriculture Chemicals Corp.*, v. *Gowan Company, L.L.C.*, Case IPR2016-00076, U.S. Pat. No. 8,791,049B2, dated Jul. 27, 2016, pp. 1-75.
Patent Owner's Motion to Amend Under 37 C.F.R 42.121, *Aceto Agriculture Chemicals Corp.*, v. *Gowan Company, L.L.C.*, Case IPR2016-00076, U.S. Pat. No. 8,791,049B2, dated Jul. 27, 2016, pp. 1-25.
Petitioner's Opposition to Patent Owner's Motion to Amend Claims of U.S. Pat. No. 8,791,049, *Aceto Agriculture Chemicals Corp.*, v. *Gowan Company, L.L.C.*, Case IPR2016-00076, U.S. Pat. No. 8,791,049B, dated Oct. 20, 2016, pp. 1-30.
Petitioner's Reply Brief in Support of Petition for *Inter Partes* Review of U.S. Pat. No. 8,791,049, *Aceto Agriculture Chemicals Corp.*, v. *Gowan Company, L.L.C.*, Case IPR2016-00076, U.S. Pat. No. 8,791,049B2, dated Oct. 20, 2016, pp. 1-31.
Patent Owner's Reply to Petitioner's Opposition to Patent Owners Motion to Amend, *Aceto Agriculture Chemicals Corp.*, v. *Gowan Company, L.L.C.*, Case IPR2016-00076, U.S. Pat. No. 8,791,049B2, dated Nov. 16, 2016, pp. 1-17.
Order: Granting Motion to Correct Inventorship, *Aceto Agriculture Chemicals Corp.*, v. *Gowan Company, L.L.C.*, Case IPR2016-00076, U.S. Pat. No. 8,791,049B2, Entered: Dec. 21, 2016, pp. 1-6.
Patent Owners Supplemental Brief Regarding Interpretation of the Claim Preamble, *Aceto Agriculture Chemicals Corp.*, v. *Gowan Company, L.L.C.*, Case IPR2016-00076, U.S. Pat. No. 8,791,049B2, dated Feb. 1, 2017, pp. 1-12.
Petitioner's Supplemental Brief Regarding the Interpretation of Preamble Statements, *Aceto Agriculture Chemicals Corp.*, v. *Gowan Company, L.L.C.*, Case IPR2016-00076, U.S. Pat. No. 8,791,049B2, dated Feb. 1, 2017, pp. 1-10.
Transcript of Oral Hearing, *Aceto Agriculture Chemicals Corp.*, v. *Gowan Company, L.L.C.*, Case IPR2016-00076, U.S. Pat. No. 8,791,049B2, Apr. 18, 2017, pp. 1-70.
Gowan Exhibit 2014, Case IPR2016-00076, Unity WDG Herbicide, dated Jul. 12, 2016, pp. 1-13.
Gowan Exhibit 2015, Case IPR2016-00076, DuPont Harmony Extra XP herbicide, dated Jul. 12, 2016, pp. 1-14.
Gowan Exhibit 2016, Case IPR2016-00076, DuPont Harmony GT XP herbicide, dated Jul. 12, 2016, pp. 1-17.
Gowan Exhibit 2017, Case IPR2016-00076, "DuPont Harmony GT XP Herbicide Harmony GT Herbicide, Pre-Plant or AT-Planting Burndown in Cotton, Field Corn, Rice, Grain, Sorghum, and Soybeans," DuPont Crop Protection, dated Jul. 12, 2016, pp. 1-2.
Gowan Exhibit 2018, Case IPR2016-00076, DuPont Matrix SG herbicide, dated Jul. 12, 2016, pp. 1-6.
Gowan Exhibit 2019, Case IPR2016-00076, Deposition of Harold Hackworth, *Aceto Agriculture Chemicals Corp.*, v. *Gowan Company, L.L.C.*, Conducted on Jul. 12, 2016, pp. 1-152.
Gowan Exhibit 2020, Case IPR2016-00076, Deposition of Robert Scott, *Aceto Agriculture Chemicals Corp.*, v. *Gowan Company, L.L.C.*, Conducted on Jul. 13, 2016, pp. 1-47.
Gowan Exhibit 2021, Case IPR2016-00076, Declaration of Eric Webster, *Aceto Agriculture Chemicals Corp.*, v. *Gowan Company, L.L.C.*, dated Jul. 27, 2016, pp. 1-99.
Gowan Exhibit 2022, Case IPR2016-00076, Declaration of Sandra Alcaraz, *Aceto Agriculture Chemicals Corp.*, v. *Gowan Company, L.L.C.*, dated Jul. 27, 2016, pp. 1-13.
Gowan Exhibit 2023, Case IPR2016-00076, Declaration of Justin B. Hensley, *Aceto Agriculture Chemicals Corp.*, v. *Gowan Company, L.L.C.*, dated Jul. 25, 2016, pp. 1-19.
Gowan Exhibit 2024, Case IPR2016-00076, DuPont Harmony Extra XP Herbicide Pre-Plant or At-Planting Burndown in Cotton, Field Corn, Grain Sorghum, Rice and Soybeans, Accepted Mar. 22, 2007, pp. 1-2.
Gowan Exhibit 2025, Case IPR2016-00076, National Pesticide Information Retrieval System-NPIRS, http://npirs.ceris.purdue.edu/htbin/view.com, last accessed Jul. 19, 2016, pp. 1-5.
Gowan Exhibit 2027, Case IPR2016-00076, InDesign/ Supported file formats for InDesign CS5, 2016, pp. 1-3.
Gowan Exhibit 2028, Case IPR2016-00076, INDD File Format, Whatls.com, last updated Jul. 2010, pp. 1-2.
Aceto Exhibit 1015, Case IPR2016-00076, Deposition of Eric Webster, Ph.D, *Aceto Agriculture Chemicals Corp.*, v. *Gowan Company, L.L.C.*, Case IPR2016-00076, U.S. Pat. No. 8,791,049B2, Sep. 23, 2016, pp. 1-139.
Aceto Exhibit 1012, Case IPR2016-00076, File History of U.S. Pat. No. 8,791,049, U.S. Appl. No. 12/966,542, filed Jul. 29, 2014, Confirmation No. 8962, pp. 1-247.
Aceto Exhibit 1013, Case IPR2016-00076, U.S. Appl. No. 60/951,300, filed Jul. 23, 2007, "Process for the Control of Undesired Vegetation," Inventor: Ronnie Helm, pp. 1-45.
Aceto Exhibit 1016, Case IPR2016-00076, Deposition of Sandra Alcaraz, *Aceto Agriculture Chemicals Corp.*, v. *Gowan Company, L.L.C.*, Case IPR2016-00076, U.S. Pat. No. 8,791,049B2, Oct. 13, 2016, pp. 1-20.
Aceto Exhibit 1017, Case IPR2016-00076, Official Filing Receipt for U.S. Appl. No. 61/287,420, filed Dec. 17, 2009, Plant Treatment Compositions Particularly Effective in the Control of *Heteranthera limosa* of Rice Crops, and Methods for Their Use, mailed Jan. 14, 2010, pp. 1-3.
Aceto Exhibit 1018, Case IPR2016-00076, ADS for U.S. Appl. No. 61/287,420, Plant Treatment Compositions Particularly Effective in the Control of *Heteranthera limosa* of Rice Crops, and Methods for Their Use, Dec. 17, 2009, pp. 1-5.
Aceto Exhibits 1020 and 1021, Case IPR2016-00076, University of Arkansas Division of Agriculture, Research Series 571, B.R. Wells, Rice Research Studies 2008, R.J. Norman, J-F. Meullenet and K.A.K Moldenhauer, Dec. 21, 2009, pp. 1-18.
Aceto Exhibit 1022, Case IPR2016-00076, view-source:arkansasagnews.uark.edu/4300.htm, Oct. 20, 2016, pp. 1-14.
Letter regarding Gowan/Aceto U.S. Pat. No. 8,791,049 dated Jun. 2, 2017, pp. 1-2.
Decision Denying Institution of *Inter Partes* Review, Case IPR2015-01016, U.S. Pat. No. 8,791,049B2, Entered Oct. 2, 2015, pp. 1-13.
Patent Owner's Preliminary Response, Case IPR2015-01016, U.S. Pat. No. 8,791,049B2, Jul. 16, 2015, pp. 1-56.
Patent Owner's Preliminary Response, Case IPR2016-00076, U.S. Pat. No. 8,791,049B2, Feb. 4, 2016, pp. 1-53.
Petition for *Inter Partes* Review of U.S. Pat. No. 8,791,049, dated Oct. 23, 2015, pp. 1-62.
Petition for *Inter Partes* Review of U.S. Pat. No. 8,791,049, dated Apr. 6, 2015, pp. 1-60.
Isaacs et al., "Rimsulfuron plus Thifensulfuron-Methyl Combinations with Selected Post-Emergence Broadleaf Herbicides in Corn (*Zea mays*)," 2002, Weed Technology, 16(3):664-668.*

* cited by examiner

PLANT TREATMENT COMPOSITIONS PARTICULARLY EFFECTIVE IN THE CONTROL OF *HETERANTHERA LIMOSA* ON RICE CROPS, AND METHODS FOR THEIR USE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

Broadly the present invention relates to an improved process for the control of undesired vegetative growth amongst rice crops, particularly Heteranthera limosa, commonly referred to as "duck salad" in rice crops.

In order to improve the crop yields of desirable crops which are used for foodstuffs, human or animal consumption, or other purposes such as biofuels it has long been the practice in the fields to utilize on the one hand a broad spectrum type of herbicide or compositions which are effective at controlling or eradicating the growth of undesired vegetation, i.e., weeds, within fields or plots having were in such crops are grown and ultimately harvested, and on the other hand to grow such crops from seeds, plants, or cultivars which have been genetically modified, crossbred, or otherwise altered in order to present specific resistance to, alternately also referred to as "tolerance to" specific classes of herbicides. Crop yields are expected to be best when a specific type or class of seed, plants, or cultivar having a specific tolerance is treated by a herbicide of that type. In such a manner, undesired vegetation growing among the plans of the crop can be controlled and or eradicated by use of the specific herbicide to which the seed, plants or cultivars exhibits resistance thereto. This is advantageous in that the farmer or other producer is not required to necessarily use two or more types of different herbicidal compounds or compositions, or to prepare multiple herbicidal preparations which may require separate applications to a crop either pre-planting, or post emergence of such herbicidal preparations to the crop.

Many classes of herbicides are also known and similarly, various suppliers have produced and made commercially available various seed lines, plants or cultivars for crops which exhibit tolerance to and/or resistance to one or more of specific classes of herbicides. For example, varieties of rice have been developed which have been genetically modified, crossbred or otherwise altered in order to exhibit resistance to one or more specific classes of herbicides.

However, while the use of certain specific classes of herbicides particularly in conjunction with rice plants known to be tolerant to the specific class or classes of herbicides, even so called "broad spectrum" herbicides are not particularly effective against further certain weeds or other undesired vegetative growth. Such requires the use of additional classes of herbicides which may on the one hand be at least partially effective against said further certain weeds or other undesired vegetative growth, but on the other hand, the use of such additional classes of herbicides increases the cost associated with growing the rice crop, increases the loading per unit growing area (e.g., acre, hectare) of herbicides which may have a negative environmental impact, and further may negatively impact the rice crop being treated, e.g., defoliation, damage, retarded growth rates, reduced crop yields per unit growing area.

One particularly pernicious undesired vegetative growth which is frequently found in the proximity or among rice plants in a rice crop is a weed commonly known as "duck salad", which is more properly identified Heteranthera limosa. Control or eradication of this weed is problematic as it is not responsive to many classes of herbicides.

Surprisingly it has been found that the incorporation of combinations of halosulfuron with thifensulfuron in treatment regimens used to control undesired vegetation in the production of rice results control of weed commonly known as "duck salad", more specifically Heteranthera limosa which are troublesome to eradicate utilizing current conventional herbicidal treatment regimens. The inventors have surprisingly discovered that the application of the combination of a halosulfuron with thifensulfuron onto rice crops unexpectedly, and it is believed synergistically provided significant control of duck salad in the crop.

Accordingly, in one aspect of the present invention, the present inventors provide improved agricultural processes for the improved cultivation of crops of rice varieties wherein the crops are treated to control undesired vegetative growth using the combination of a halosulfuron with thifensulfuron to provide improved herbicidal efficacy, particularly herbicidal efficacy against "duck salad", more specifically Heteranthera limosa which is present in a rice crop. Indeed the efficacy of the combined the combination of a halosulfuron with thifensulfuron in such an application is believed to provide an unexpected and synergistic benefit/

In a second aspect of the invention, the present inventors provide improved agricultural processes for the improved cultivation of crops of rice varieties wherein the crops are treated to control undesired vegetative growth using the combination of a halosulfuron with thifensulfuron to provide improved herbicidal efficacy, particularly herbicidal efficacy against "duck salad", more specifically Heteranthera limosa wherein the said composition is application prior to the emergence of the rice crop, and/or prior to planting of the rice crop.

According to a third aspect of the invention there are provided new regimens for the herbicidal treatment of rice crops in order to provide improved undesired vegetative growth within the planted rice crop.

According to a fourth aspect of the invention, there are provided herbicidal compositions which are particularly useful in the treatment of crops of rice varieties according to the processes or regimens of the first, second or third aspects of the invention.

These and other aspects of the invention will become more apparent from the following description.

Practice of certain aspects of the present invention contemplate the use of plant treatment composition which necessarily comprises the combination of a halosulfuron with thifensulfuron and which plant treatment composition may optionally further include one or more further constituents. Such further constituents may be biologically active materials, e.g., materials which exhibit or provide pesticidal, disease control, including fungicidal, mildew control or herbicidal or plant growth regulating effects, or may be non-biologically active materials, e.g. solvents, carriers, surfactants, and the like.

The treatment compositions, and processes utilizing the treatment compositions of the invention necessarily require the combination of a halosulfuron with thifensulfuron to be applied either preemergence, or applied post emergence to a rice crop to provide eradication, or control of "duck salad", more specifically Heteranthera limosa. The said the combination of a halosulfuron with thifensulfuron thereof may be applied in any effective amount which is observed to be satisfactory to provide a desired degree of control, or which provides effective eradication of Heteranthera limosa.

The present inventors have discovered that plant treatment compositions comprising the combination of a halosulfuron with thifensulfuron are particularly useful in the treatment of plants rice crops to provide a desired degree of control, or which provides effective eradication of Heteranthera limosa. The degree of efficacy of control of Heteranthera limosa is believed to be syngergistic.

The halosulfuron useful in the various aspects of the invention may be described as halosulfuron-based herbicides, specifically a halosulfuron methyl which may be represented by the structure:

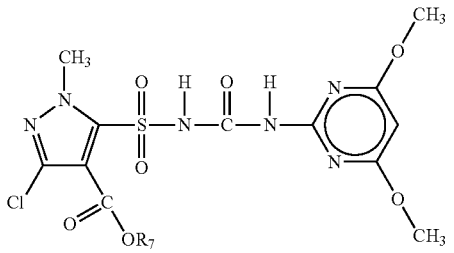

Wherein $R_7$ is hydrogen or is a $C_1$-$C_6$ straight or branched alkyl group, preferably is hydrogen, methyl or ethyl but in a particularly preferred embodiment $R_7$ is methyl, and the resultant compound (in an acid form) is sometimes identified as methyl, 3-chloro-5-(4,6-dimethoxypyrimidin-2-ylcarbamoylsulfamoyl)-1-methylpyrazole-4-carboxylic acid. The foregoing compound wherein $R_7$ is hydrogen also referred to in this specification by its brief tradename "PERMIT" (es. Gowan Co.) which is prominent member of halosulfuron-methyl compounds having herbicidal properties. Salts or acids of the above halosulfuron-methyl compounds may also be used.

The thifensulfuron useful in the various aspects of the invention may be described as

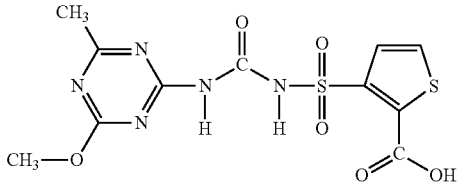

which compound is also known as thifensulfuron or thifensulfuron-methyl. This compound is also known as to the art as 3-(4-methoxy-6-methyl-1,3,5-triazin-2-ylcarbamoylsulfamoyl)thiophene-2-carboxylic acid. Salts or acids of the foregoing compound may also be used.

In certain and preferred aspects of the invention, the use of one or more further herbicidal treatment compounds, compositions or preparations are contemplated; such one or more further herbicidal treatment compounds are referred to as "co-herbicides"

The combination of a halosulfuron with thifensulfuron may be applied independently of any further co-herbicide constituent in an application step forming part of a treatment regimen or alternately the said combination of a halosulfuron with thifensulfuron may be applied concurrently with one or more further co-herbicide constituents in an application step forming part of a treatment regimen. The said combination of a halosulfuron with thifensulfuron may be applied with one or more further materials or constituents other than a co-herbicide but independently of any further co-herbicide constituent in an application step forming part of a treatment regimen or alternately the said combination of a halosulfuron with thifensulfuron may be applied concurrently with one or more further materials or constituents other than a co-herbicide as well with one or more further co-herbicide constituents in an application step forming part of a treatment regimen.

The amounts of combination of a halosulfuron with thifensulfuron in the plant treatment compositions of the invention may vary widely and in part, depend upon the form of the product of the plant treatment compositions. Generally speaking the combination of a halosulfuron with thifensulfuron may be provided in amounts of as little as 0.000001% wt. to as much as 100% wt (0.01 ppm to 1,000,000 ppm). of the plant treatment composition of which it forms a part. For example, higher concentrations are to be expected wherein the form of the plant treatment composition is a concentrate or super-concentrate composition which is provided to a user such as a plant grower with instructions to form a dilution in a liquid or solid carrier, e.g., water or other solvent, prior to application to plants. Lesser concentrations are expected wherein the plant treatment composition is provided as a ready-to-use product which is intended to be dispensed directly without further dilution from any container onto a plant. The plant treatment compositions of the invention may be applied "neat" in water, or as part of a "tank mix" with other materials or constituents.

The respective weight ratios of halosulfuron to thifensulfuron provided in a combination of a halosulfuron with thifensulfuron, and/or as may be ultimately present in a plant treatment composition "as applied" onto a plant, plant part, or crop, particularly a rice crop may vary within specific limits. Advantageously the respective weight ratio of halosulfuron to thifensulfuron in the form a plant treatment composition in an ultimate form "as applied" or ready to be applied, viz., not requiring further dilution, is preferably in the range of from 4:3 of halosulfuron to thifensulfuron, more preferably in the range of from 1:0.125, yet more preferably 0.66:0.08, and especially preferably the ultimate respective relative weight ratios of is as disclosed in one or more of the Examples.

Advantageously, the ultimate end-use concentration of the combination of a halosulfuron with thifensulfuron in the plant treatment compositions, viz., the concentration in the plant treatment compositions which are in the form as applied to seeds, plants or for that matter soil, are those which are found to be effective in the treatment of a rice crop, which amount is understood to be variable, as it may be affected by many factors, including but not limited to: treatment dosages and application rates, weather and seasonal conditions experienced during the plant or crop growing cycle, etc. Such variables are which are commonly encountered by and understood by the skilled artisan, who may make adjustments to the treatment regimen, e.g., application rate, and/or application timings and/or application frequencies.

The inventors have also surprisingly discovered that the combination of halosulfuron to thifensulfuron, particularly in the preferred respective weight ratios and further preferably at preferred application rates show surprisingly good efficacy against a weed commonly known as "duck salad", which is more properly identified Heteranthera limosa. Control or eradication of this weed is problematic as it is not responsive to many classes of herbicides. It is noted that degree of efficacy is not attained with another combination, namely halosulfuron with tribenuron, as is more clearly disclosed with reference to the comparative Examples discussed later.

Although it is contemplated that while the plant treatment compositions of the invention may be provided in a powdered or pulvurent form, it is expected that the plant treatment compositions are provided in a liquid, gel, foam or paste form. The plant treatment compositions are advantageously provided in a liquid carrier system, e.g., in an aqueous or other fluid carrier which permits for the convenient mixing of a measured quantity of a concentrated form of the plant treatment compositions with a larger volume of water or other fluid carrier in which the concentrated form is diluted, such as in forming a tank mix. Alternately, the plant treatment compositions may be provided in a form such that no further dilution is required and such plant treatment compositions may be used directly in the treatment of plants.

While it may be convenient to combine both the halosulfuron and the thifensulfuron in a single product which may be either in a ready-to-use format and not require further dilution or mixing, or which may be provided in a concentrated format which require further mixing with further other constituents and/or require dilution with a liquid carrier in order to form the ultimate form of the plant treatment composition, e.g. "tank mix", such is not an essential requirement. Thus, it is contemplated that prior to use or application to a crop or plants, the plant treatment composition may be provided in two or more parts, one containing the halosulfuron and optionally one or more further biologically active and/or non-biologically active constituents, and another part containing the thifensulfuron and optionally one or more further biologically active and/or non-biologically active constituents, which two or more parts are combined, and further optionally further diluted in a carrier or solvent, e.g. water, in order to form the ultimate plant treatment composition ready to be applied.

Thus according to certain embodiments, in one aspect, the present invention provides plant treatment compositions which include combinations of halosulfuron and thifensulfuron, and a liquid carrier, preferably a liquid carrier which is water or which is a largely aqueous liquid carrier, with the proviso that the plant treatment compositions exclude biologically active materials which exhibit or provide pesticidal, disease control, including fungicidal, mildew control or herbicidal or plant growth regulating effects.

According to yet further preferred embodiment, in a further aspect, the present invention provides plant treatment compositions which include combinations of halosulfuron and thifensulfuron in combination with a liquid carrier, preferably a liquid carrier which is water or which is a largely aqueous liquid carrier, with the proviso that the plant treatment compositions also exclude co-herbicides, but may include one or more further other biologically active materials.

In addition to the essential combination of halosulfuron and thifensulfuron as disclosed above, the plant treatment compositions of the invention may include one or more further additional optional constituents which may be used to provide one or more further technical effects or benefits to the plant treatment compositions.

The plant treatment compositions of invention may optionally include one or more constituents or materials especially such as further biologically active materials, e.g., materials which exhibit or provide pesticidal, disease control, including fungicidal, mildew control or herbicidal or plant growth regulating effects, as well as one or more non-biologically active materials.

By way of nonlimiting examples, examples of biologically active materials include materials which exhibit or provide pesticidal, disease control, including fungicidal, mildew control or herbicidal or plant growth regulating effects Exemplary fungicides which may be used in the plant treatment compositions of the invention include one or more of: 2-phenylphenol; 8-hydroxyquinoline sulfate; AC 382042; Ampelomyces quisqualis; Azaconazole; Azoxystrobin; Bacillus subtilis; Benalaxyl; Benomyl; Biphenyl; Bitertanol; Blasticidin-S; Bordeaux mixture; Borax; Bromuconazole; Bupirimate; Calboxin; calcium polysulfide; Captafol; Captan; Carbendazim; Carpropanmid (KTU 3616); CGA 279202; Chinomethionat; Chlorothalonil; Chlozolinate; copper hydroxide; copper naphthenate; copper oxychloride; copper sulfate; cuprous oxide; Cymoxanil; Cyproconazole; Cyprodinil; Dazomet; Debacarb; Dichlofluanid; Dichlomezine; Dichlorophen; Diclocymet; Diclorán; Diethofencarb; Difenoconazole; Difenzoquat; Difenzoquat metilsulfate; Diflumetorim; Dimethirimol; Dimethomorph; Diniconazole; Diniconazole-M; Dinobuton; Dinocap; diphnenylamine; Dithianon; Dodemorph; Dodemorph acetate; Dodine; Dodine free base; Edifenphos; Epoxiconazole (BAS 480F); Ethasulfocarb; Ethirimol; Etridiazole; Famoxadone; Fenamidone; Fenarimol; Fenbuconazole; Fenfin; Fenfuram; Fenhexamid; Fenpiclonil; Fenpropidin; Fenpropimorph; Fentin acetate; Fentin hydroxide; Ferbam; Ferimzone; Fluazinam; Fludioxonil; Fluoroimide; Fluquinconazole; Flusilazole; Flusulfamide; Flutolanil; Flutriafol; Folpet; formaldehyde; Fosetyl; Fosetyl-aluminum; Fuberidazole; Furalaxyl; Fusarium oxysporum; Gliocladium virens; Guazatine; Guazatine acetates; GY-81; hexachlorobenzene; Hexaconazole; Hymexazol; ICIA0858; IKF-916; Imazalil; Imazalil sulfate; Imibenconazole; Iminoctadine; Iminoctadine triacetate; Iminoctadine tris[Albesilate]; Ipconazole; Iprobenfos; Iprodione; Iprovalicarb; Kasugamycin; Kasugamycin hydrochloride hydrate; Kresoxim-methyl; Mancopper; Mancozeb; Maneb; Mepanipyrim; Mepronil; mercuric chloride; mercuric oxide; mercurous chloride; Metalaxyl; Metalaxyl-M; Metam; Metam-sodium; Metconazole; Methasulfocarb; methyl isothiocyanate; Metiram; Metominostrobin (SSF-126); MON65500; Myclotbutanil; Nabam; naphthenic acid; Natamycin; nickel bis(dimethyldithiocarbamate); Nitrothalisopropyl; Nuarimol; Octhilinone; Ofurace; oleic acid (fatty acids); Oxadixyl; Oxine-copper; Oxycarboxin; Penconazole; Pencycuron; Pentachlorophenol; pentachlorophenyl laurate; Perfurazoate; phenylmercury acetate; Phlebiopsis gigantea; Phthalide; Piperalin; polyoxin B; polyoxins; Polyoxorim; potassium hydroxyquinoline sulfate; Probenazole; Prochloraz; Procymidone; Propamocarb; Propamocarb Hydrochloride; Propiconazole; Propineb; Pyrazophos; Pyributicarb; Pyrifenox; Pyrimethanil; Pyroquilon; Quinoxyfen; Quintozene; ISH-7281; sec-butylamine; sodium 2-phenylphenoxide; sodium pentachlorophenoxide; Spiroxamine (KWG 4168); Streptomyces griseoviridis; sulfur; tar oils; Tebuconazole; Tecnazene; Tetraconazole; Thiabendazole; Thifluzawide; Thiophanate-methyl; Thiram; Tolclofos-methyl; Tolylfluanid; Triadimefon; Triadimenol; Triazoxide; Trichoderma harzianum; Tricyclazole; Tridemorph; Triflumizole; Triforine; Triticonzole; Validamycin; vinclozolin; zinc naphthenate; Zineb; Ziram; the compounds having the chemical name methyl (E,E)-2-(2-(1-(1-(2-pyridyl)propyloxyimino)-1-cyclopropylmethyloxymethyl)$_p$ henyl)-3-ethoxypropenoate and 3-(3,5-dichlorophenyl)-4-chloropyrazole.

When present the one or more fungicides, may be included in any effective amount, and advantageously are present in amounts of from 1 ppm to 50,000 ppm, preferably 10 ppm to 10,000 ppm based on total weight of the plant treatment composition of which it forms a part, as applied to the plant. The concentration of such one or more fungicides will of course be expected to be higher when present in a concentrated form of the composition of the invention, e.g., a concentrate form which is supplied to the ultimate user of the produce, e.g. grower, wherein such a concentrate is intended to be diluted in a liquid and/or solid carrier, e.g., largely aqueous tank mixes wherein the dilution ratio of the concentrate form to the liquid and/or solid carrier is intended to provide a plant treatment composition to be used directly upon plants or crops.

Exemplary pesticides include insecticides, acaricides and nematocides, which be used singly or in mixtures in the plant treatment compositions of the invention. By way of non-limiting example such include one or more of: Abamectin; Acephate; Acetamiprid; oleic acid; Acrinathrin; Aldicarb; Alanycarb; Allethrin [(1R) isomers]; .alpha.-Cypermethrin; Amitraz; Avermectin B1 and its derivatives, Azadirachtin; Azamethiphos; Azinphos-ethyl; Azinphosmethyl; Bacillus thurigiensi; Bendiocarb; Benfuracarb; Bensultap; .beta.-cyfluthrin; .beta.-cypermethrin; Bifenazate; Bifenthrin; Bioallathrin; Bioallethrin (S-cyclopentenyl isomer); Bioresmethrin; Borax; Buprofezin; Butocarboxim; Butoxycarboxim; piperonyl butoxide; Cadusafos; Carbaryl; Carbofuran; Carbosulfan; Cartap; Cartap hydrochloride; Chordane; Chlorethoxyfos; Chlorfenapyr; Chlorfenvimphos; Chlorfluazuron; Chlormephos; Chloropicrin; Chlorpyrifos; Chlorpyrifos-methyl; mercurous chloride; Coumaphos; Cryolite; Cryomazine; Cyanophos; calcium cyanide; sodium cyanide; Cycloprothrin; Cyfluthrin; Cyhalothrin; cypermethrin; cyphenothrin [(1R) transisomers]; Dazomet; DDT; Deltamethrin; Demeton-5-methyl; Diafenthiuron; Diazinon; ethylene dibromide; ethylene dichloride; Dichlorvos; Dicofol; Dicrotophos; Diflubenzuron; Dimethoate; Dimethylvinphos; Diofenolan; Disulfoton; DNOC; DPX-JWO62 and DP; Empenthrin [(EZ)-(1R) isomers]; Endosulfan; ENT 8184; EPN; Esfenvalerate; Ethiofencarb; Ethion; Ethiprole having the chemical name 5-amino-3-cyano-1-(2,6-dichloro-4-trifluoromethylphenyl)-4-ethylsulfinylpyrazole; Ethoprophos; Etofenprox; Etoxazole; Etrimfos; Famphur; Fenamiphos; Fenitrothion; Fenobucarb; Fenoxycarb; Fenpropathrin; Fenthion; Fenvalerate; Fipronil and the compounds of the arylpyrazole family; Flucycloxuron; Flucythrinate; Flufenoxuron; Flufenprox; Flumethrin; Fluofenprox; sodium fluoride; sulfuryl fluoride; Fonofos; Formetanate; Formetanate hydrochloride; Formothion; Furathiocarb; Gamma-HCH; GY-81; Halofenozide; Heptachlor; Heptenophos; Hexaflumuron; sodium hexafluorosilicate; tar oils; petroleum oils; Hydramethylnon; hydrogen cyanide; Hydroprene; Imidacloprid; Imiprothrin; Indoxacarb; Isazofos; Isofenphos; Isoprocarb; Methyl isothiocyanal; Isoxathion; lambda-Cyhalothrin; pentachlorophenyl laurate; Lufenuron; Malathion; MB-599; Mecarbam; Methacrifos; Methamidophos; Methidathion; Methiocarb; Methomyl; Methoprene; Methoxychlor; Metolcarb; Mevinphos; Milbemectin and its derivatives; Monocrotophos; Naled; nicotine; Nitenpyram; Nithiazine; Novaluron; Omethoate; Oxamyl; Oxydemeton-methyl; Paecilomyces fumosoroseus; Parathion; Parathion-methyl; pentachlorophenol; sodium pentachlorophenoxide; Permethrin; Penothrin [(1R)-trans-isomers]; Phenthoate; Phorate; Phosalone; Phosmet; Phosphamidon; phosphine; aluminum phosphide; magnesium phosphide; zinc phosphide; Phoxim; Pirimicarb; Pirimiphos-ethyl; Pirimiphos-methyl; calcium polysulfide; Prallethrin; Profenfos; Propaphos; Propetamphos; Propoxur; Prothiofos; Pyraclofos; pyrethrins (chrysanthemates, pyrethrates, pyrethrum; Pyretrozine; Pyridaben; Pyridaphenthion; Pyrimidifen; Pyriproxyfen; Quinalphos; Resmethrin; RH-2485; Rotenone; RU 15525; Silafluofen; Sulcofuron-sodium; Sulfotep; sulfuramide; Sulprofos; Ta-fluvalinate; Tebufenozide; Tebupirimfos; Teflubenzuron; Tefluthrin; Temephos; Terbufos; Tetrachlorvinphos; Tetramethrin; Tetramethrin [(1R) isomers]; .theta.-cypermethrin; Thiametoxam; Thiocyclam; Thiocyclam hydrogen oxalate; Thiodicarb; Thiofanox; Thiometon; Tralomethrin; Transfluthrin; Triazamate; Triazophos; Trichlorfon; Triflumuron; Trimethacarb; Vamidothion; XDE-105; XMC; Xylylcarb; Zeta-cypermethrin; ZXI 8901; the compound whose chemical name is 3-acetyl-5-amino-1-[2,6-dichloro-4-(trifluoromethyl)phenyl]-2-methylsulfinylpyrazole.

When present the one or more pesticides, may be included in any effective amount, and advantageously are present in amounts of from 5 ppm to 50,000 ppm, preferably 10 ppm to 10,000 ppm based on total weight of the plant treatment composition of which it forms a part, particularly in final end-use concentrations of the plant treatment compositions as applied to the plant.

Exemplary herbicides which may be used as co-herbicides in the plant treatment compositions of the invention, may include one or more of: 2,3,6-TBA; 2,4-D; 2,4-D-2-ethylhexyl; 2,4-DB; 2,4-DB-butyl; 2,4-DB-dimethylammonium; 2,4-DB-isooctyl; 2,4-DB-potassium; 2,4-DB-sodium; 2,4-D-butotyl (2,4-D-Butotyl (2,4-D Butoxyethyl Ester)); 2,4-D-butyl; 2,4-D-dimethylammonium; 2,4-D-Diolamine; 2,4-D-isoctyl; 2,4-D-isopropyl; 2,4-D-sodium; 2,4-D-trolamine; Acetochlor; Acifluorfen; Acifluorfen-sodium; Aclonifen; Acrolein; AKH-7088; Alachlor; Alloxydim; Alloxydim-sodium; Ametryn; Amidosulfuron; Amitrole; ammonium sulfamate; Anilofos; Asulam; Asulam-sodium; Atrazine; Azafenidin; Azimsulfuron; Benazolin; Benazolin-ethyl; Benfluralin; Benfuresate; Benoxacor; Bensulfuron; Bensulfuron-methyl; Bensulide; Bentazone; Bentazone-sodium; Benofenap; Bifenox; Bilanofos; Bilanafos-sodium; Bispyribac-sodium; Borax; Bromacil; Bromobutide; Bromofenoxim; Bromoxynil; Bromoxynil-heptanoate; Bromoxynil-octanoate; Bromoxynil-potassium, Butachlor; Butamifos; Butralin; Butroxydim; butylate; Cafenstrole; Carbetamide; Carfentrazone-ethyl; Chlomethoxyfen; Chloramben; Chlorbromuron; Chloridazon; Chlorimuron; Chlorimuron-ethyl; Chloroacetic Acid; Chlorotoluron; Chlorpropham; Chlorsulfuron; Chlorthal; Chlorthal-dimethyl; Chlorthiamid; Cinmethylin; Cinosulfuron; Clethodim; Clodinafop; Clodinafop-Propargyl; Clomazone; Clomeprop; Clopyralid; Clopyralid-Olamine; Cloquintocet; Cloquintocet-Mexyl; Chloransulam-methyl; CPA; CPA-dimethylammonium; CPA-isoctyl; CPA-thioethyl; Cyanamide; Cyanazine; Cycloate; Cyclosulfamuron; Cycloxydim; Cyhalofop-butyl; Daimuron; Dalapon; Dalapon-sodium; Dazomet; Desmeduipham; Desmetryn; Dicamba; Dicamba-dimethylammonium; Dicamba-potassium; Dicamba-sodium; Dicamba-trolamine; Dichlobenil; Dichlormid; Dichlorprop; Dichlorprop-butotyl (Dichlorprop-butotyl (Dichlorpropbutoxyethyl ester)); Dichlorpropdimethylammonium; Dichlorprop-isoctyl; Dichlorprop-P; Dichlorprop-potassium; Diclofop; Diclofop-methyl; Difenzoquat; Difenzoquat metilsulfate; Diflufenican; Diflufenzopyr (BAS 654 00 H); Dimefuron; Dimepiperate; Dimethachlor; Dimethametryn; Dimethenamid; Dimethipin; dimethylarsinic acid; Dinitramine; Dinoterb; Dinoterb acetate; Dinoterb-ammonium; Dinoterb-diolamine; Diphenamid; Diquat; Diquat dibromide; Dithiopyr; Diuron; DNOC; DSMA; Endothal; EPTC; Esprocarb; Ethalfluralin; Ethametsulfuron-methyl; Ethofumesate; Ethoxysulfuron; Etobenzanid; Fenchlorazole-ethyl; Fenclorim; Fenoxaprop-P; Fenoxaprop-P-ethyl; Fenuron; Fenuron-TCA; Ferrous Sulfate; Flamprop-M; Flamprop-M-Isopropyl; Flamprop-M-methyl; Flazasulfuron; Fluazifop; Fluazifop-butyl; Fluazifop-P; Fluazifop-P-butyl; Fluazolate; Fluchloralin; Flufenacet (BAS FOE 5043); Flumetsulam; Flumiclorac; Flumiclorac-Pentyl; Flumioxazin; Fluometuron; Fluoroglycofen; Fluoroglycofen-ethyl; Flupaxam; Flupoxam; Flupropanate; Flupropanate-sodium; Flupyrsulfuron-methyl-sodium; Flurazole; Flurenol; Flurenol-butyl; Fluridone; Fluorochloridone; Fluoroxypyr; Fluoroxypyr-2-Butoxy-1-methylethyl; Fluoroxypyr-methyl; Flurtamone; Fluthioacetmethyl; Fluxofenim; Fomesafen; Fomesafen-sodium; Fosamine; Fosamine-ammonium; Furilazole; Glyphosate; Glufosinate; Glufosinate-ammonium; Glyphosate-ammonium; Glyphosate-isopropylammonium; Glyphosate-sodium; Glyphosate-trimesium; Haloxyfop; Haloxyfop-P-methyl; Haloxyfop-etotyl; Haloxyfop-methyl; Hexazinone; Hilanafos; Imazacluin; Imazamethabenz; Imazamox; Imazapyr; Imazapyr-isopropylammonium; Imazaquin; Imazaquin-ammonium; Imazemethabenz-methyl; Imazethapyr; Imazethapyr-ammonium; Imazosulfuron; Imizapic (AC 263,222); Indanofan; Ioxynil; Ioxynil octanoate; Ioxynil-sodium; Isoproturon; Isouron; Isoxaben; Isoxaflutole; Lactofen; Laxynel octanoate; Laxynil-sodium; Lenacil; Linuron; MCPA; MCPA-butotyl; MCPA-dimethylammonium; MCPA-isoctyl; MCPA-potassium; MCPA-sodium; MCPA-thioethyl; MCPB; MCPB-ethyl; MCPB-sodium; Mecoprop; Mecoprop-P; Mefenacet; Mefenpyr-diethyl; Mefluidide; Mesulfuron-methyl; Metam; Metamitron; Metam-sodium; Metezachlor; Methabenzthiazuron; methyl isothiocyanate; methylarsonic acid; Methyldymron; Metobenzuron; Metobromuron; Metolachlor; Metosulam; Metoxuron; Metribuzin; Metsulfuron; Molinate; Monolinuron; MPB-sodium; MSMA; Napropamide; Naptalam; Naptalam-sodium; Neburon; Nicosulfuron; nonanoic acid; Norflurazon; oleic acid (fatty acids); Orbencarb; Oryzalin; Oxabetrinil; Oxadiargyl; Oxasulfuron; Oxodiazon; Oxyfluorfen; Paraquat; Paraquat Dichloride; Pebulate; Pendimethalin; Pentachlorophenol; Pentachlorophenyl Laurate; Pentanochlor; Pentoxazone; petroleum oils; Phenmedipham; Picloram; Picloram-potassium; Piperophos; Pretilachlor; Primisulfuron; Primisulfuron-methyl; Prodiamine; Prometon; Prometryn; Propachlor; Propanil; Propaquizafop; Propazine; Propham; Propisochlor; Propyzamide; Prosulfocarb; Prosulfuron; Pyraflufen-ethyl; Pyrazasulfuron; Pyrazolynate; Pyrazosulfuron-ethyl; Pyrazoxyfen; Pyribenzoxim; Pyributicarb; Pyridate; Pyriminobac-methyl; Pyrithiobac-sodium; Quinclorac; Quinmerac; Quinofolamine; Quizalofop; Quizalofop-ethyl; Quizalofop-P; Quizalofop-P-ethyl; Quizalofop-P-Tefuryl; Rimsulfuron; Sethoxydim; Siduron; Simazine; Simetryn; sodium chlorate; sodium chloroacetate; sodium pentachlorophenoxide; sodium-Dimethylarsinate; Sulcotrione; Sulfentrazone; Sulfometuron; Sulfometuron-methyl; Sulfosulfuron; Sulfuric acid; tars; TCA-sodium; Tebutam; Tebuthiuron; Tepraluxydim (BAS 620H); Terbacil; Terbumeton; Terbuthylazine; Terbutryn; Thenylchlor; Thiazopyr; Thiobencarb; Tiocarbazil; Tralkoxydim; triallate; Triasulfuron; Triaziflam; Tribenuron; Tribenuron-methyl; Tribenuron-methyl; trichloroacetic acid; Triclopyr; Triclopyr-butotyl; Triclopyr-triethylammonium; Trietazine; Trifluralin; Triflusulfuron; Triflusulfuron-methyl; Vemolate: YRC 2388.

When present the one or more co-herbicides, may be included in any effective amount, and advantageously are present in amounts of from 5 ppm to 50,000 ppm, preferably 10 ppm to 10,000 ppm based on total weight of the plant treatment composition of which it forms a part, particularly in ultimate end-use concentrations of the plant treatment compositions as applied.

The composition of the invention may further contain one or more non-biologically active materials which include, but are not limited to one or more of: a surfactant, a solvent, a safener, a binder, a stabilizer, a dye, a fragrance material, a synergist, a phytotoxicity reducer, a pH buffer, a pH adjusting agent, and a lubricant according to the requirements.

Non-limiting examples of surfactants useful in the plant treatment compositions of the invention include one or more of anionic, nonionic, cationic, amphoteric and zwitterionic surfactants, which can be used singly or in mixtures. Exemplary nonionic surfactants include polyoxyethylene alkyl ethers, polyoxyethylene alkyl allyl ethers, polyoxyethylene lanolin alcohols, polyoxyethylene alkyl phenol formalin condensates, polyoxyethylene sorbitan fatty acid esters, polyoxyethylene glycerol mono-fatty acid esters, polyoxypropylene glycol mono-fatty acid esters, polyoxyethylene sorbitol fatty acid esters, polyoxyethylene-castor oil derivatives, polyoxyethylene fatty acid esters, fatty acid glycerol esters, sorbitan fatty acid esters, sucrose fatty acid esters, polyoxyethylene polyoxypropylene block polymers, polyoxyethylene fatty acid amides, alkylol amides, and polyoxyethylene alkyl amines; aminonic surfactants include sodium salts of fatty acids such as sodium palmitate, ether sodium carboxylates such as polyoxyethylene lauryl ether sodium carboxylate, amino acid condensates of fatty acids such as lauroyl sodium sarcosine and N-lauroyl sodium glutamate, alkylarylsulfonates such as sodium dodecylbenzenesulfonate and diisopropylnaphthalenesulfonates, fatty acid ester sulfonates such as lauric acid ester sulfonates, dialkyl sulfosuccinates such as dioctyl sulfosuccinate, fatty acid amidosulfonates such as oleic acid amidosulfonate, formalin condensates of alkylarylsulfonates, alcohol sulfates such as pentadecane-2-sulfate, polyoxyethylene alkyl ether sulfates such as polyoxyethylene dodecyl ether sodium sulfate, polyoxyethylene alkyl phosphates such as dipolyoxyethylene dodecyl ether phosphates, styrene-maleic acid copolymers, and alkyl vinyl ether-maleic acid copolymers; and amphoteric surfactants such as N-laurylalanine, N,N,N-trimethylaminopropionic acid, N,N,N-trihydroxye thylaminopropionic acid, N-hexyl N,N-dimethylaminoacetic acid, 1-(2-carboxyethyl)-pyridiniumbetaine, and lecithin; exemplary cationic surfactants include alkylamine hydrochlorides such as dodecylamine hydrochloride, benzethonium chloride, alkyltrimethylammoniums such as dodecyltrimethylammonium, alkyldimethylbenzylammoniums, alkylpyridiniums, alkylisoquinoliniums, dialkylmorpholiniums, and polyalkylvinylpyridiniums.

Non-limiting examples of solvents useful in the plant treatment compositions of the invention include one or more of saturated aliphatic hydrocarbons such as: decane, tridecane, tetradecane, hexadecane, and octadecane; unsaturated aliphatic hydrocarbons such as 1-undecene and 1-henicosene; halogenated hydrocarbons; ketones such as acetone and methyl ethyl ketone; alcohols such as methanol, ethanol, butanol, and octanol; esters such as ethyl acetate, dimethyl phthalate, methyl laurate, ethyl palmitate, octyl acetate, dioctyl succinate, and didecyl adipate; aromatic hydrocarbons such as xylene, ethylbenzene, octadecylbenzene, dodecylnaphthalene, tridecylnaphthalene; glycols, glycol esters, and glycol ethers such as ethylene glycol, diethylene glycol, propylene glycol monomethyl ether, and ethyl cellosolve; glycerol derivatives such as glycerol and glycerol fatty acid ester; fatty acids such as oleic acid, capric acid, and enanthic acid; polyglycols such as tetraethylene glycol, polyethylene glycol, and polypropylene glycol; amides such as N,N-dimethylformamide and diethylformamide: animal and vegetable oils such as olive oil, soybean oil, colza oil, castor oil, linseed oil, cottonseed oil, palm oil, avocado oil, and shark oil; as well as mineral oils. Water and blends of water with one or more of the foregoing organic solvents are also expressly contemplated as being useful solvent constituents.

Non-limiting examples of stabilizers which may be used in the invention are one or more of antioxidants, light stabilizers, ultraviolet stabilizers, radical scavengers, and peroxide decomposers. Examples of the antioxidant are antioxidants of phenol type, amine type, phosphorus type, and sulfur type antioxidants. Examples of the ultraviolet stabilizer are that of benzotriazole type, cyanoacrylate type, salicylic acid type, and hindered amine type. Isopropyl acid phosphate, liquid paraffin, and epoxidized vegetable oils like epoxidized soybean oil, linseed oil, and colza oil may also be used as the stabilizer.

Each of the foregoing non-biologically active materials which may be individually included in effective amounts. The total amounts of the one or more non-biologically active materials may be as little as 0.001% wt., to as much as 99.999% wt., based on the total weight of the plant treatment composition of which said non-biologically active materials form a part, particularly in the ultimate, or final end-use concentrations of the plant treatment compositions as applied to the plant.

The plant treatment compositions can be advantageously applied as leaf, stem, root, into-water, seed dressing, nursery box or soil treatment compositions. Thus the plant treatment compositions of the invention can be applied to the seed, soil, preemergence, as well as post-emergence such as directly onto immature or mature plants, particularly rice plants The plant treatment compositions of the invention can be applied according to conventional application techniques known to the art, including electrodynamic spraying techniques. While not wishing to be bound by the following, it is hypothesized that at least the metal alginate salts are deposited and are retained on the plant matter surfaces after the carrier, viz., aqueous medium or aqueous organic solvent medium has evaporated.

The plant treatment compositions may be provided in a variety of product forms. In one such form a concentrated composition containing the combination of halosulfuron and thifensulfuron are provided in a form wherein the concentrated composition is intended to be blended or dispersed in a further fluid carrier such as water or other largely aqueous liquid, either without further biologically active materials or conjointly with one or more further biologically active materials, viz., materials which exhibit or provide pesticidal, disease control, including fungicidal, mildew control or herbicidal or plant growth regulating effects, as well as any other further desired biologically inactive constituents which are recognized as being a useful in the art. In a further product form, the plant treatment compositions of the invention are provided as a ready to use product wherein the combination of halosulfuron and thifensulfuron are provided in the said composition at a concentration which requires no further dilution but can be directly applied to plants, or crops, viz., as a ready to use composition. In a still further product form, the combination of halosulfuron and thifensulfuron are provided in conjunction with one or more further biologically active materials, e.g., materials which exhibit or provide pesticidal, disease control, including fungicidal, mildew control or herbicidal or plant growth regulating effects, as well as any other further desired biologically inactive constituents, in the form of a premix, or in the form of a concentrate which is intended to be added to further the carrier medium, such as an aqueous liquid which may, or may not include further constituents already present therein.

The plant treatment composition may also be provided in a powdered or solid form, e.g., a comminuted solid which can be dispersed into a fluid carrier or medium, in a concentrated form, which may be a solid, liquid, or a gel which is intended to be further dissolved or dispersed in a carrier medium, such as a liquid which may be pressurized or non-pressurized, e.g., water. Such a plant treatment composition is advantageously and conveniently provided as a dispersible or dilutable concentrate composition which is then used in a "tank mix" which may optionally include further compositions or compounds, including but not limited to biologically active materials and non-biologically active materials.

The plant treatment compositions of the invention may also be provided in any suitable or conventional packaging means. For example, conventional containers such as bottles, or sachets containing a solid, liquid or fluid composition enclosed within a water-soluble film or water soluble capsule may be conveniently provided particularly when the former are provided in premeasured unit dosage forms. The latter are particularly useful in avoiding the need for measuring or packaging and provides a convenient means whereby specific doses that the plant treatment compositions can be provided.

The plant treatment compositions according to the invention may also be effective in controlling further undesired vegetative growth which may be found in rice crops e.g.: spiny Amaranth (Amaranth spinosus) barnyard grass (Echinochloa crusgalli), bindweed (Calystegia sepium), Burcucumber (Sicyas angulatus), California Arrowhead (Sagittaria montevidensis) common Cocklebur (Xanthium strumarium), Corn Spurry (Spergula arvensis), wooly Cupgrass (Eriochloa villosa), Dayflower (Commelina erecta), Dogbane Hemp, (Apocynum cannabinum), Eclipta (Ecilpta prostrata), rice flatsedge (Cyperus iria), Philadelphia Fleabane (Erigeron philadelphicus), Foxtail, giant, yellow, green, bristly (Galinsoga) Golden Crownbeard (Verbesina encliodes), Goosefoot Groundsel, common (Senecio vulgaris), Horsenettle, (Solanum carolinense), Horseweed/Marestail (Erigeron Canadensis), Horsetail (Equisetum), Jimsonweed (Datura stramonium), Itchgrass (Rottboellia cochinchinensis), Jointvetch (Aeschynomene), Johnsongrass rhizome, seedling (Sorghum halepense), Kochia (Kochia scoparia), Ladysthumb (Polygonum persicaria), Lambsquarter, common (Chenoposium album), Mallow, Venice (Hibiscus trionum), common Milkweed (Asclepias syriaca), honeyvine Milkweed (Ampelamus albidus), Millet, Wild Proso (Paniucum miliaceum), Morningglory, Ivyleaf (Ipomoea hederacea), Tall Morningglory (Ipomoea purppurea), wild Mustard (Sinapis arevensis), Black Nightshade (Solanum americanum), yellow Nutsedge (Cyperus exculentus), purple Nutsedge (Cyperus rotundus), oats, Fall Panicum (Paniucm dichotomiflorum), Texas Panicum (Panicum texanum), Maypop Passionflower (Passiflora incarnate), Redroot Pigweed (Amarunthus retroffiexus), smooth Pigweed (Amaranthus hybridus), common Pokeweed (Phytolacca Americana), Purslane (Portulaca oleracea), Quackgrass (Elytrigia repense), wild Radish (Rapharius raphanistrum), common Ragweed (Ambrosia artemisiifolia), giant Ragweed (Ambrosia trifida), Redstem (Ammania auriculata), Ricefield Bulrush (Scirpus mucronatus), Italian Ryegrass (Lollum multiflorum), Sandbur, Sesbania, Hemp (Sesbania exaltata), Shattercane (Sorghum bilcolor) Signalgrass, broadleaf, Shepherdspurse (capsella bursa-pastoris (L.) medicus), prickly Sida, Smallflower Umbrellaplant, Pennsylvania smartweed (Polyfonum pensylvanisum), Sorghum Almum, Canada Thistle (Cirsium arvense), Sunflower (Helianthus annuus) and Velvetleaf (Abutilan theophrasti).

The following examples below illustrate exemplary formulations as well as preferred embodiments of the invention. It is to be understood that these examples are provided by way of illustration only and that further useful formulations falling within the scope of the present invention and the claims may be readily produced by one skilled in the art without deviating from the scope and spirit of the invention.

EXAMPLES

A number of separate test areas were used to evaluate the efficacy of certain treatment regimens for the control of undesired vegetative growth, more specifically, the control of Heteranthera limosa, commonly referred to as "duck salad" in a rice crop planted with rice. The following Table illustrates the efficacy of plant treatment compositions according to the invention which included combination of halosulfuron and thifensulfuron, as well as comparative examples which did not include the combination of halosulfuron and thifensulfuron. The former are identified by a digit prefixed by the letter "E", the latter comparative examples by a digit prefixed by the letter "C" in the Table. The identity of the constituents and timings of application of are as indicated following. The tests were performed in Louisiana, USA at a controlled facility, during the growth of the crop Heteranthera limosa, commonly referred to as "duck salad" was observed to be prevalent amongst the rice plants of the rice crop. The compositions in each of the examples were formed as tank mixes in water, and applied to the rice crop utilizing a backpack mounted hand held sprayer, pressurized with $CO_2$.

In the following table, the "NIS" indicates a non-ionic surfactant, and "COC" indicates a crop oil concentrate.

TABLE

| | | | | % control of Heteranthera limosa | | % damage to treated rice crops | |
|---|---|---|---|---|---|---|---|
| Example: | Treatment regimen | Application rate (actives) | Growth stage of crop at application(s) | Evaluation at 8 days post emergence | Evaluation at 20 days post emergence | Evaluation at 8 days post emergence | Evaluation at 20 days post emergence |
| C1 (control) | --none-- | — | — | 0% | 0% | 0% | 0% |
| C2 | (a) PERMIT; and, (b) PERMIT + NIS | (a) PERMIT at 0.0314 lb active/acre; and, (b) PERMIT at 0.0314 lb active/acre + NIS at 0.25% v/v per acre | (a) preemergence; and; (b) 10-14 days post emergence | 81% | 74% | 0% | 0% |
| C3 | (a) PERMIT + tribenuron; and, (b) PERMIT + tribenuron + NIS | (a) PERMIT at 0.0314 lb active/acre + tribenuron at 0.008 active/acre; and, (b) PERMIT at 0.0314 lb active/acre + tribenuron at 0.008 active/acre NIS at 0.25% v/v per acre | (a) preemergence; and; (b) 10-14 days post emergence | 94% | 71% | 10% | 8% |

| | | | | % control of Heteranthera limosa | | |
|---|---|---|---|---|---|---|
| Example: | Treatment regimen | Application rate (actives) | Growth stage of crop at application(s) | Evaluation at 7 days post emergence | Evaluation at 14 days post emergence | Evaluation at 26 days post emergence |
| C4 | (a) PERMIT + COC; and, (b) PERMIT + COC | each (a) and (b) both: PERMIT at 0.67 oz active/acre + 19.2 fluid oz. COC per acre | (a) preemergence; and; (b) 10-14 days post emergence | 69% | 78% | 43% |
| C5 | (a) thifensulfuron + COC; and, | each (a) and (b) both: thifensulfuron at | (a) preemergence; and; (b) 10-14 days post | 71% | 66% | 23% |

TABLE-continued

| | | | | | | |
|---|---|---|---|---|---|---|
| | (b) thifensulfuron + COC | 0.08 oz active/acre + 19.2 fluid oz. COC per acre | emergence | | | |
| C6 | (a) thifensulfuron + COC; and, (b) thifensulfuron + COC | each (a) and (b) both: thifensulfuron at 0.3 oz active/acre + 19.2 fluid oz. COC per acre | (a) preemergence; and; (b) 10-14 days post emergence | 91% | 95% | 55% |
| C7 | thifensulfuron + COC | thifensulfuron at 0.08 oz active/acre + 19.2 fluid oz. COC per acre | preemergence | 55% | 61% | 20% |
| C8 | thifensulfuron + COC | thifensulfuron at 0.08 oz active/acre + 19.2 fluid oz. COC per acre | 10-14 days post emergence | 44% | 41% | 30% |

| | | | | % control of Heteranthera limosa | | % damage to treated rice crops | |
|---|---|---|---|---|---|---|---|
| Example: | Treatment regimen | Application rate (actives) | Growth stage of crop at application(s) | Evaluation at 8 days post emergence | Evaluation at 20 days post emergence | Evaluation at 8 days post emergence | Evaluation at 20 days post emergence |
| E1 | (a) PERMIT + thifensulfuron; and, (b) PERMIT + thifensulfuron + NIS | (a) PERMIT at 0.0314 lb active/acre + thifensulfuron at 0.0038 lb active/acre; and, (b) PERMIT at 0.0314 lb active/acre + thifeunsulfuron at 0.0038 lb active/acre + NIS at 0.25% v/v per acre | (a) preemergence; and; (b) 10-14 days post emergence | 92% | 93% | 10% | 0% |
| E2 | (a) PERMIT + thifensulfuron; and, (b) PERMIT + thifensulfuron + NIS | (a) PERMIT at 0.0314 lb active/acre + thifensulfuron at 0.014 lb active/acre; and, (b) PERMIT at 0.0314 lb active/acre + thifeunsulfuron at 0.014 lb active/acre + NIS at 0.25% v/v per acre | (a) preemergence; and; (b) 10-14 days post emergence | 90% | 94% | 0% | 0% |

| | | | | % control of Heteranthera limosa | | |
|---|---|---|---|---|---|---|
| Example: | Treatment regimen | Application rate (actives) | Growth stage of crop at application(s) | Evaluation at 7 days post emergence | Evaluation at 14 days post emergence | Evaluation at 26 days post emergence |
| E3 | (a) PERMIT + thifensulfuron + COC; and, (b) PERMIT + thifensulfuron + COC | each (a) and (b) were: PERMIT at 0.67 oz active/acre + thifensulfuron at 0.08 oz. active/acre + 19.2 fluid oz. COC per acre | (a) preemergence; and; (b) 10-14 days post emergence | 94% | 96% | 63% |
| E4 | (a) PERMIT + thifensulfuron + COC; and, (b) PERMIT + thifensulfuron + COC | each (a) and (b) were: PERMIT at 0.67 oz active/acre + thifensulfuron at 0.3 oz. active/acre + 19.2 fluid oz. COC per acre | (a) preemergence; and; (b) 10-14 days post emergence | 93% | 98% | 73% |
| E5 | (a) PERMIT + thifensulfuron + COC; and, (b) PERMIT + thifensulfuron + COC | each (a) and (b) were: PERMIT at 0.67 oz active/acre + thifensulfuron at 0.08 oz. active/acre + 19.2 fluid oz. COC per acre | (a) preemergence; and; (b) 10-14 days post emergence | 95% | 96% | 60% |

TABLE-continued

| | | | | | | |
|---|---|---|---|---|---|---|
| E6 | (a) PERMIT + thifensulfuron + COC; and, (b) PERMIT + thifensulfuron + COC | each (a) and (b) were: PERMIT at 0.67 oz active/acre + thifensulfuron at 0.08 oz. active/acre + 19.2 oz. COC per acre | (a) preemergence; and; (b) 10-14 days post emergence | 91% | 98% | 70% |
| E7 | PERMIT + thifensulfuron + COC | PERMIT at 0.67 oz active/acre + thifensulfuron at 0.08 oz. active/acre + 19.2 fluid oz. COC per acre | preemergence | 60% | 69% | 28% |
| E8 | PERMIT + thifensulfuron + COC | PERMIT at 0.67 oz active/acre + thifensulfuron at 0.08 oz. active/acre + 19.2 fluid oz. COC per acre | 10-14 days post emergence | 46% | 40% | 25% |

With reference to the constituents identified in the foregoing Table,

PERMIT=

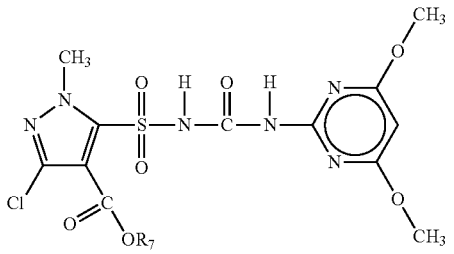

wherein $R_7$ is methyl.

NIS=a nonionic surfactant.

COC=supplied as Agridex (ex. Helena Chem. Co.)

thifensulfuron=

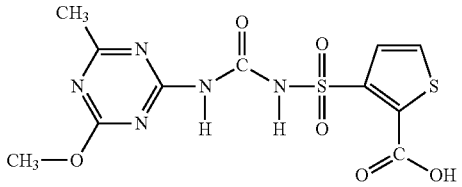

tribenuron=

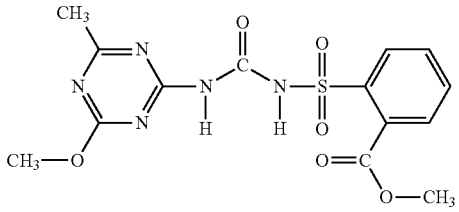

The results reported on the table are evaluations which were performed based on visual evaluation of like-sized areas of each of the treated rice plots which like-sized areas were randomly selected. The Table reports both the % control or the degree of control of undesired vegetative growth of Heteranthera limosa in the evaluated areas of each of the rice crops, demonstrating the efficacy of the E1 and E2 plant compositions, compared to the plant treatment composition of the comparative examples, namely the untreated control C1, as well as further comparative treatment regimens C2 and C3. The observed and results reported results are surprising and would be unexpected by a skilled artisan, suggesting a synergistic benefit of the combination of halosulfuron and thifensulfuron in the plant treatment composition. It was also observed that sulfonylurea based herbicide treatment preparations did not deleteriously affect the crop of the rice varieties tested.

Surprisingly the substitution of a further triazinylsulfonulurea herbicide, viz., tribenuron-methyl for the thifensulfuron as per C3 provided significantly poorer control of Heteranthera limosa especially 20 days post application than plant treatment compositions and regimens according to the invention, namely E1 and E2. Such illustrates the unexpected nature of the specific combination of the claimed inventive plant treatment compositions.

The benefits of this discovery are real and are several. As is readily seen from the foregoing, it is contemplated that the use of combination of halosulfuron and thifensulfuron may provide similarly effective and surprisingly good control of Heteranthera limosa which could not be previously attained with prior art compositions. Further, the foregoing suggests that the use of combination of halosulfuron and thifensulfuron provides highly effective control or eradiction of Heteranthera limosa at lower net application rates using the use of combination of halosulfuron and thifensulfuron than might be otherwise required using other herbicidal compounds other than the disclosed specific use of combination of halosulfuron and thifensulfuron taught herein. Both of the above provide for simultaneous control, with decreased loadings of herbicidal compounds applied to unit areas of crops (e.g., acre, hectare), thus permitting improved crop harvest yields per unit area, with reduced loadings of herbicides per said unit area, therefore also providing an important environmental benefit.

The invention claimed is:

1. An agricultural process for the improved cultivation of rice wherein the crops are treated to control undesired vegetative growth using a plant treatment composition comprising both halosulfuron and thifensulfuron in synergistically effective amounts in order to provide improved herbicidal efficacy against Heteranthera limosa present in rice crops, the process comprising the step of:

applying the said plant treatment composition to rice crops to control against Heteranthera limosa which may be present in the rice crops.

2. A process according to claim 1 wherein the synergistically effective amounts of halosulfuron to thifensulfuron is a weight ratio of about 4:3 of halosulfuron to thifensulfuron in a plant treatment composition as applied to the rice crop.

3. A process according to claim 1, wherein the synergistically effective amounts of halosulfuron to thifensulfuron is a weight ratio of about 1:0.125 of halosulfuron to thifensulfuron in a plant treatment composition as applied to the rice crop.

4. A process according to claim 1, wherein the synergistically effective amounts of halosulfuron to thifensulfuron is a weight ratio of about 0.66:0.08 of halosulfuron to thifensulfuron in a plant treatment composition as applied to the rice crop.

5. A process according to claim 1, wherein the plant treatment composition additionally comprises a biologically active material which exhibits or provides pesticidal, herbicidal, disease control, fungicidal, mildew control, or plant growth regulating effects.

6. Plant treatment compositions for providing herbicidal efficacy against Heteranthera limosa present in rice crops, wherein said plant treatment compositions comprise synergistically effective amounts of both halosulfuron and thifensulfuron.

7. A plant treatment composition according to claim 6, wherein the synergistically effective amounts of halosulfuron to thifensulfuron is a respective weight ratio of about 4:3 in the plant treatment composition as applied to the rice crop.

8. A plant treatment composition according to claim 6, wherein the synergistically effective amounts of halosulfuron to thifensulfuron is a respective weight ratio of about 1:0.125 in the plant treatment composition as applied to the rice crop.

9. A plant treatment composition according to claim 6, wherein the synergistically effective amounts of halosulfuron to thifensulfuron is a respective weight ratio of about 0.66:0.08 in the plant treatment composition as applied to the rice crop.

10. A plant treatment composition according to claim 6, wherein the plant treatment composition additionally comprises a biologically active material which exhibits or provides pesticidal, herbicidal, disease control, fungicidal, mildew control or plant growth regulating effects.

11. A plant treatment composition according to claim 6 wherein the halosulfuron is represented by the following structure:

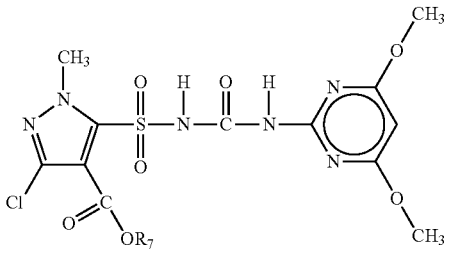

wherein $R_7$ is hydrogen or is a $C_1$-$C_6$ straight or branched alkyl group.

12. A plant treatment composition according to claim 11, wherein $R_7$ is hydrogen, methyl or ethyl.

13. A plant treatment composition according to claim 12 wherein the halosulfuron is methyl, 3-chloro-5-(4,6-dimethoxypyrimidin-2-ylcarbamoylsulfamoyl)-1-methylpyrazole-4-carboxylic acid.

14. A plant treatment composition according to claim 6 wherein the thifensulfuron is represented by the following structure:

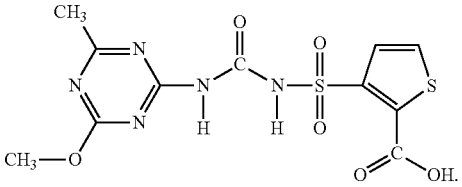

15. A process according to claim 1, wherein the synergistically effective amounts of halosulfuron to thifensulfuron is a weight ratio of about 22.42-2.23:1 of halosulfuron to thifensulfuron in the plant treatment composition as applied to the rice crop.

16. A process according to claim 15, wherein the synergistically effective amounts of halosulfuron to thifensulfuron is a weight ratio of about 8.37-2.23:1 of halosulfuron to thifensulfuron in the plant treatment composition as applied to the rice crop.

17. A process according to claim 1, wherein the plant treatment composition is applied to a rice crop at the following stages of growth: (a) preemergent, and (b) 10-14 days post emergence.

18. A process according to claim 15, wherein the plant treatment composition is applied to a rice crop at the following stages of growth: (a) preemergent, and (b) 10-14 days post emergence.

19. A process according to claim 1, wherein the plant treatment composition comprises halosulfuron, thifensulfuron and a liquid carrier, and which composition excludes further biologically active materials which exhibit or provide pesticidal, disease control, fungicidal, mildew control, herbicidal or plant growth regulating effects.

20. A process according to claim 1, wherein the synergistically effective amounts of halosulfuron to thifensulfuron is a weight ratio range of about 1:0.12-1:1.2 of halosulfuron to thifensulfuron in a plant treatment composition as applied to the rice crop.

21. A process according to claim 1, wherein in the plant treatment composition comprising both halosulfuron and thifensulfuron the synergistically effective amounts of the halosulfuron and thifensulfuron is any combination of thifensulfuron methyl with halosulfuron methyl which, when compared to either an otherwise like composition having a like amount of thifensulfuron methyl but without halosulfuron methyl being present, or a like composition having a like amount of halosulfuron methyl but without thifensulfuron methyl being present.

*22. A method for controlling undesired vegetative growth in a rice crop comprising applying a plant treatment composition comprising halosulfuron and thifensulfuron to rice crops to control against undesired vegetative growth that may be present in the rice crops, wherein the weight ratio of halosulfuron to thifensulfuron is 8.37:1.*

*23. The method of claim 22, wherein the undesired vegetative growth is spiny Amaranth (Amaranth spinosus), barnyard grass (Echinochloa crusgalli), bindweed (Calystegia sepium), Burcucumber (Sicyas angulatus), California Arrowhead (Sagittaria montevidensis), common Cocklebur (Xanthium strumarium), Corn Spurry (Spergula arvensis), wooly Cupgrass (Eriochloa villosa), Dayflower (Commelina erecta), Dogbane Hemp, (Apocynum cannabinum), Eclipta*

(*Ecilpta prostrata*), *rice flatsedge* (*Cyperus iria*), *Philadelphia Fleabane* (*Erigeron philadelphicus*), *Foxtail*, (*Galinsoga*), *Golden Crownbeard* (*Verbesina encliodes*), *Goosefoot, Groundsel, common* (*Senecio vulgaris*), *Horsenettle*, (*Solanum carolinense*), *Horseweed/Marestail* (*Erigeron Canadensis*), *Horsetail* (*Equisetum*), *Jimsonweed* (*Datura stramonium*), *Itchgrass* (*Rottboellia cochinchinensis*), *Jointvetch* (*Aeschynomene*), *Johnsongrass rhizome, seedling* (*Sorghum halepense*), *Kochia* (*Kochia scoparia*), *Ladysthumb* (*Polygonum persicaria*), *Lambsquarter, common* (*Chenoposium album*), *Mallow, Venice* (*Hibiscus trionum*), *common Milkweed* (*Asclepias syriaca*), *honeyvine Milkweed* (*Ampelamus albidus*), *Millet, Wild Proso* (*Paniucum miliaceum*), *Morningglory, Ivyleaf* (*Ipomoea hederacea*), *Tall Morningglory* (*Ipomoea purppurea*), *wild Mustard* (*Sinapis arevensis*), *Black Nightshade* (*Solanum americanum*), *yellow Nutsedge* (*Cyperus exculentus*), *purple Nutsedge* (*Cyperus rotundus*), *oats, Fall Panicum* (*Paniucm dichotomiflorum*), *Texas Panicum* (*Panicum texanum*), *Maypop Passionflower* (*Passiflora incarnate*), *Redroot Pigweed* (*Amarunthus retroffiexus*), *smooth Pigweed* (*Amaranthus hybridus*), *common Pokeweed* (*Phytolacca Americana*), *Purslane* (*Portulaca oleracea*), *Quackgrass* (*Elytrigia repense*), *wild Radish* (*Rapharius raphanistrum*), *common Ragweed* (*Ambrosia artemisiifolia*), *giant Ragweed* (*Ambrosia trifida*), *Redstem* (*Ammania auriculata*), *Ricefield Bulrush* (*Scirpus mucronatus*), *Italian Ryegrass* (*Lollum multiflorum*), *Sandbur, Sesbania, Hemp* (*Sesbania exaltata*), *Shattercane* (*Sorghum bilcolor*) *Signalgrass, broadleaf, Shepherdspurse* (*capsella bursa-pastoris* (*L.*) *medicus*), *prickly Sida, Smallflower Umbrellaplant, Pennsylvania smartweed* (*Polyfonum pensylvanisum*), *Sorghum Almum, Canada Thistle* (*Cirsium arvense*), *Sunflower* (*Helianthus annuus*) *or Velvetleaf* (*Abutilan theophrasti*).

*24. The method of claim 22, wherein the undesired vegetative growth is Amaranth* (*Amaranth spinosus*), *barnyard grass* (*Echinochloa crusgalli*), *bindweed* (*Calystegia sepium*), *Burcucumber* (*Sicyas angulatus*), *common Cocklebur* (*Xanthium strumarium*), *Corn Spurry* (*Spergula arvensis*), *Eclipta* (*Ecilpta prostrata*), *rice flatsedge* (*Cyperus iria*), *Philadelphia Fleabane* (*Erigeron philadelphicus*), (*Galinsoga*), *Golden Crownbeard* (*Verbesina encliodes*), *Goosefoot, Groundsel, Horsenettle*, (*Solanum carolinense*), *Horseweed/Marestail* (*Erigeron Canadensis*), *Horsetail* (*Equisetum*), *Jimsonweed* (*Datura stramonium*), *Jointvetch* (*Aeschynomene*), *Kochia* (*Kochia scoparia*), *Ladysthumb* (*Polygonum persicaria*), *Lambsquarter, common* (*Chenoposium album*), *Mallow, Venice* (*Hibiscus trionum*), *common Milkweed* (*Asclepias syriaca*), *honeyvine Milkweed* (*Ampelamus albidus*), *Morningglory, Ivyleaf* (*Ipomoea hederacea*), *Tall Morningglory* (*Ipomoea purppurea*), *wild Mustard* (*Sinapis arevensis*), *yellow Nutsedge* (*Cyperus exculentus*), *purple Nutsedge* (*Cyperus rotundus*), *Maypop Passionflower* (*Passiflora incarnate*), *Redroot Pigweed* (*Amarunthus retroffiexus*), *smooth Pigweed* (*Amaranthus hybridus*), *common Pokeweed* (*Phytolacca Americana*), *Purslane* (*Portulaca oleracea*), *wild Radish* (*Rapharius raphanistrum*), *common Ragweed* (*Ambrosia artemisiifolia*), *giant Ragweed* (*Ambrosia trifida*), *Redstem* (*Ammania auriculata*), *Ricefield Bulrush* (*Scirpus mucronatus*), *Sesbania, Hemp* (*Sesbania exaltata*), *Shepherdspurse* (*capsella bursa-pastoris* (*L.*) *medicus*), *prickly Sida, Smallflower Umbrellaplant, Sunflower* (*Helianthus annuus*) *or Velvetleaf* (*Abutilan theophrasti*).

*25. The method of claim 22, wherein the composition excludes further biologically active materials which exhibit or provide pesticidal, disease control, fungicidal, mildew control, herbicidal or plant growth regulating effects.*

*26. The method of claim 23, wherein the composition excludes further biologically active materials which exhibit or provide pesticidal, disease control, fungicidal, mildew control, herbicidal or plant growth regulating effects.*

*27. The method of claim 24, wherein the composition excludes further biologically active materials which exhibit or provide pesticidal, disease control, fungicidal, mildew control, herbicidal or plant growth regulating effects.*

*28. The process of claim 1, wherein the synergistically effective amounts of halosulfuron to thifensulfuron is a weight ratio of 8.37:1 of halosulfuron to thifensulfuron in a plant treatment composition as applied to the rice crop.*

*29. A method for controlling undesired vegetative growth in a rice crop comprising applying a plant treatment composition comprising halosulfuron and thifensulfuron to rice crops to control against undesired vegetative growth that may be present in the rice crops, wherein the plant treatment compositions are applied post-emergence.*

*30. The method of claim 22, wherein the undesired vegetative growth is Amaranth* (*Amaranth spinosus*), *barnyard grass* (*Echinochloa crusgalli*), *Bindweed* (*Calystegia sepium*), *Burcucumber* (*Sicyas angulatus*), *Common Cocklebur* (*Xanthium strumarium*), *Corn Spurry* (*Spergula arvensis*), *Eclipta* (*Ecilpta prostrata*), *Rice Flatsedge* (*Cyperus iria*), *Philadelphia Fleabane* (*Erigeron philadelphicus*), (*Galinsoga*), *Golden Crownbeard* (*Verbesina encliodes*), *Goosefoot, Groundsel, Horsenettle*, (*Solanum carolinense*), *Horseweed/Marestail* (*Erigeron Canadensis*), *Horsetail* (*Equisetum*), *Jimsonweed* (*Datura stramonium*), *Jointvetch* (*Aeschynomene*), *Kochia* (*Kochia scoparia*), *Ladysthumb* (*Polygonum persicaria*), *Common Lambsquarter* (*Chenoposium album*), *Venice Mallow* (*Hibiscus trionum*), *Common Milkweed* (*Asclepias syriaca*), *Honeyvine Milkweed* (*Ampelamus albidus*), *Ivyleaf Morningglory* (*Ipomoea hederacea*), *Tall Morningglory* (*Ipomoea purppurea*), *Wild Mustard* (*Sinapis arevensis*), *Yellow Nutsedge* (*Cyperus exculentus*), *Purple Nutsedge* (*Cyperus rotundus*), *Maypop Passionflower* (*Passiflora incarnate*), *Redroot Pigweed* (*Amarunthus retroffiexus*), *Smooth Pigweed* (*Amaranthus hybridus*), *Common Pokeweed* (*Phytolacca Americana*), *Purslane* (*Portulaca oleracea*), *Wild Radish* (*Rapharius raphanistrum*), *Common Ragweed* (*Ambrosia artemisiifolia*), *Giant Ragweed* (*Ambrosia trifida*), *Redstem* (*Ammania auriculata*), *Ricefield Bulrush* (*Scirpus mucronatus*), *Hemp Sesbania* (*Sesbania exaltata*), *Shepherdspurse* (*capsella bursa-pastoris* (*L.*) *medicus*), *Prickly Sida, Smallflower Umbrellaplant, Sunflower* (*Helianthus annuus*) *or Velvetleaf* (*Abutilan theophrasti*).

*31. The method of claim 29, wherein the weight ratio of halosulfuron to thifensulfuron is 8.37-8:1.*

*32. The method of claim 29, wherein the composition is applied at a rate of 0.06-0.30 oz thifensulfuron/acre.*

*33. The method of claim 29, wherein the composition excludes further biologically active materials which exhibit or provide pesticidal, disease control, fungicidal, mildew control, herbicidal or plant growth regulating effects.*

*34. A method for controlling undesired vegetative growth in a rice crop comprising applying a plant treatment composition comprising halosulfuron and thifensulfuron to rice crops to control against undesired vegetative growth that may be present in the rice crops, wherein the weight ratio of halosulfuron to thifensulfuron is 8.37-8:1.*

*35. The method of claim 34, wherein the undesired vegetative growth is Amaranth* (*Amaranth spinosus*), *Barnyardgrass* (*Echinochloa crusgalli*), *Bindweed* (*Calystegia*

*sepium), Burcucumber (Sicyas angulatus), Common Cocklebur (Xanthium strumarium), Corn Spurry (Spergula arvensis), Eclipta (Ecilpta prostrata), Rice Flatsedge (Cyperus iria), Philadelphia Fleabane (Erigeron philadelphicus), (Galinsoga), Golden Crownbeard (Verbesina encliodes), Goosefoot, Groundsel, Horsenettle, (Solanum carolinense), Horseweed/Marestail (Erigeron Canadensis), Horsetail (Equisetum), Jimsonweed (Datura stramonium), Jointvetch (Aeschynomene), Kochia (Kochia scoparia), Ladysthumb (Polygonum persicaria), Common Lambsquarter (Chenoposium album), Venice Mallow (Hibiscus trionum), Common Milkweed (Asclepias syriaca), Honeyvine Milkweed (Ampelamus albidus), Ivyleaf Morningglory (Ipomoea hederacea), Tall Morningglory (Ipomoea purppurea), Wild Mustard (Sinapis arevensis), Yellow Nutsedge (Cyperus exculentus), Purple Nutsedge (Cyperus rotundus), Maypop Passionflower (Passiflora incarnate), Redroot Pigweed (Amarunthus retroffiexus), Smooth Pigweed (Amaranthus hybridus), Common Pokeweed (Phytolacca Americana), Purslane (Portulaca oleracea), Wild Radish (Rapharius raphanistrum), Common Ragweed (Ambrosia artemisiifolia), Giant Ragweed (Ambrosia trifida), Redstem (Ammania auriculata), Ricefield Bulrush (Scirpus mucronatus), Hemp Sesbania (Sesbania exaltata), Shepherdspurse (capsella bursapastoris (L.) medicus), Prickly Sida, Smallflower Umbrellaplant, Sunflower (Helianthus annuus) or Velvetleaf (Abutilan theophrasti).*

*36. The method of claim 34, wherein the composition excludes further biologically active materials which exhibit or provide pesticidal, disease control, fungicidal, mildew control, herbicidal or plant growth regulating effects.*

*37. The method of claim 29, further comprising applying a composition comprising halosulfuron and thifensulfuron before said rice crop emerges.*

*38. A method for controlling undesired vegetative growth in a rice crop comprising applying a composition comprising halosulfuron and thifensulfuron to rice crops to control against undesired vegetative growth that may be present in the rice crops, wherein halosulfuron and thifensulfuron are the only herbicides in said composition.*

*39. The method of claim 38, wherein the undesired vegetative growth is Amaranth (Amaranth spinosus), Barnyardgrass (Echinochloa crusgalli), Bindweed (Calystegia sepium), Burcucumber (Sicyas angulatus), Common Cocklebur (Xanthium strumarium), Corn Spurry (Spergula arvensis), Eclipta (Ecilpta prostrata), Rice Flatsedge (Cyperus iria), Philadelphia Fleabane (Erigeron philadelphicus), (Galinsoga), Golden Crownbeard (Verbesina encliodes), Goosefoot, Groundsel, Horsenettle, (Solanum carolinense), Horseweed/Marestail (Erigeron Canadensis), Horsetail (Equisetum), Jimsonweed (Datura stramonium), Jointvetch (Aeschynomene), Kochia (Kochia scoparia), Ladysthumb (Polygonum persicaria), Common Lambsquarter (Chenoposium album), Venice Mallow (Hibiscus trionum), Common Milkweed (Asclepias syriaca), Honeyvine Milkweed (Ampelamus albidus), Ivyleaf Morningglory (Ipomoea hederacea), Tall Morningglory (Ipomoea purppurea), Wild Mustard (Sinapis arevensis), Yellow Nutsedge (Cyperus exculentus), Purple Nutsedge (Cyperus rotundus), Maypop Passionflower (Passiflora incarnate), Redroot Pigweed (Amarunthus retroffiexus), Smooth Pigweed (Amaranthus hybridus), Common Pokeweed (Phytolacca Americana), Purslane (Portulaca oleracea), Wild Radish (Rapharius raphanistrum), Common Ragweed (Ambrosia artemisiifolia), Giant Ragweed (Ambrosia trifida), Redstem (Ammania auriculata), Ricefield Bulrush (Scirpus mucronatus), Hemp Sesbania (Sesbania exaltata), Shepherdspurse (capsella bursapastoris (L.) medicus), Prickly Sida, Smallflower Umbrellaplant, Sunflower (Helianthus annuus) or Velvetleaf (Abutilan theophrasti).*

*40. The method of claim 38, wherein the weight ratio of halosulfuron to thifensulfuron is 8.37-8:1.*

*41. The method of claim 38, wherein the composition is applied at a rate of 0.06-0.30 oz thifensulfuron/acre.*

*42. A plant treatment composition comprising halosulfuron and thifensulfuron, wherein halosulfuron and thifensulfuron are the only herbicides in said composition.*

*43. The plant treatment composition of claim 42, wherein the weight ratio of halosulfuron to thifensulfuron is 8.37-8:1.*

* * * * *